US011543393B2

(12) United States Patent
Beckers et al.

(10) Patent No.: US 11,543,393 B2
(45) Date of Patent: Jan. 3, 2023

(54) GAS CHROMATOGRAPHY COLUMN WITH POLYBUTADIENE COATING

(71) Applicant: KONINKLIJKE PHILIPS N.V., Eindhoven (NL)

(72) Inventors: Lucas Johannes Anna Maria Beckers, Veldhoven (NL); Johan Hendrik Klootwijk, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 602 days.

(21) Appl. No.: 16/495,156

(22) PCT Filed: Mar. 20, 2018

(86) PCT No.: PCT/EP2018/056951
§ 371 (c)(1),
(2) Date: Sep. 18, 2019

(87) PCT Pub. No.: WO2018/172320
PCT Pub. Date: Sep. 27, 2018

(65) Prior Publication Data
US 2020/0033305 A1 Jan. 30, 2020

Related U.S. Application Data

(60) Provisional application No. 62/473,551, filed on Mar. 20, 2017.

(51) Int. Cl.
*G01N 30/02* (2006.01)
*G01N 30/60* (2006.01)
(Continued)

(52) U.S. Cl.
CPC ..... *G01N 30/6095* (2013.01); *G01N 33/0009* (2013.01); *G01N 33/497* (2013.01);
(Continued)

(58) Field of Classification Search
CPC ................. G01N 2030/025; G01N 2030/8854
See application file for complete search history.

(56) References Cited

U.S. PATENT DOCUMENTS 3,538,744 A * 11/1970 Karasek ................. G01N 30/92
73/23.4
3,983,299 A * 9/1976 Regnier ............. B01J 20/28078
427/301
(Continued)

FOREIGN PATENT DOCUMENTS

EP 0307530 A1 * 9/1989
JP 2006329777 A 12/2006
(Continued)

OTHER PUBLICATIONS

J. Klein, et al., "Mixed-Polymeric Stationary Hases in Gas Chromatography", Journal of Polymer Science: Plymer Symposium, vol. 68, pp. 221-228.
(Continued)

*Primary Examiner* — Lisa M Caputo
*Assistant Examiner* — Alex T Devito

(57) ABSTRACT

A 3D gas chromatography (GC) column development is possible by assembly of two parts each being substrates formed by gas tight materials. One part may be a silicon substrate with a snake shaped flow channel structure and the other part may be a glass plate. Both are coated with a column packing comprising polubutadiene, which is also able to glue or bond both parts together, thereby sealing the flow channel, thus forming a GC column. The column packaging can be composed in all kinds of polarity from very hydrophobic till very hydrophilic. In this way the column packing can be tuned on resolution for particular molecules which are interesting to detect, e.g. Octane. The invention is advantageous for micro GC columns.

20 Claims, 4 Drawing Sheets

(51) Int. Cl.
  *G01N 33/00* (2006.01)
  *G01N 33/497* (2006.01)
  *G01N 30/88* (2006.01)

(52) U.S. Cl.
  CPC ......... *G01N 2030/025* (2013.01); *G01N 2030/8813* (2013.01); *G01N 2030/8854* (2013.01)

(56) References Cited

U.S. PATENT DOCUMENTS

| | | | |
|---|---|---|---|
| 4,990,458 A * | 2/1991 | Rosenfeld | G01N 30/06 560/204 |
| 2002/0158022 A1 | 10/2002 | Huang | |
| 2006/0120683 A1 | 6/2006 | Kamp et al. | |
| 2011/0250626 A1 | 10/2011 | Williams et al. | |
| 2011/0294677 A1 | 12/2011 | Beckers | |
| 2014/0157867 A1 | 6/2014 | Kim | |

FOREIGN PATENT DOCUMENTS

| | | |
|---|---|---|
| WO | 9215385 A1 | 9/1992 |
| WO | 2005032688 A1 | 4/2005 |

OTHER PUBLICATIONS

International Search Report and Written Opinion, International Application No. PCT/EP2018/056951, dated Jun. 26, 2018.

Liu, J. et al., "Smart multi-channel two-dimensional micro-gas chromatography for rapid workplace hazardous volatile organic compounds measurement", Lab on a Chip, vol. 13, No. 5, Dec. 2012.

Ligor, M. et al., "Determination of volatile organic compounds in exhaled breath of patients with lung cancer using solid phase microextraction and gas chromatography mass spectrometry", Clinical Chemistry and Laboratory Medicine, vol. 47, No. 5, May 2009.

Schnecko, H. et al., "Terminally Reactive Liquid Polymers as Stationary Phases for Gas Chromatography", Angewandte Makromolekulare Chemie (Now: Macromolecular Materials and Engineering), vol. 20 (1); 1971; p. 111-119.

* cited by examiner

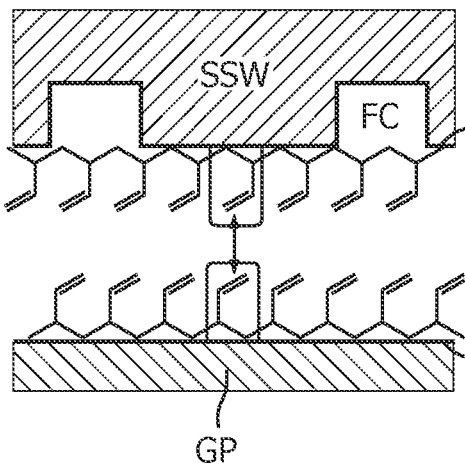
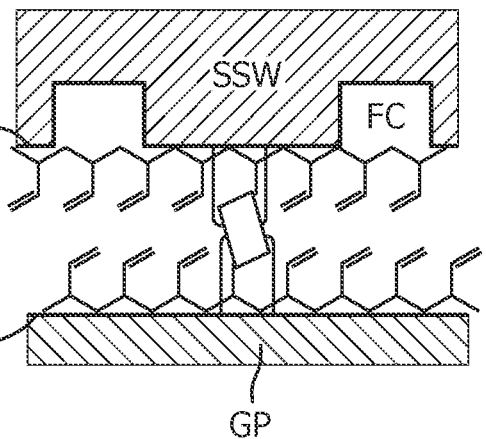
FIG. 5a    FIG. 5b
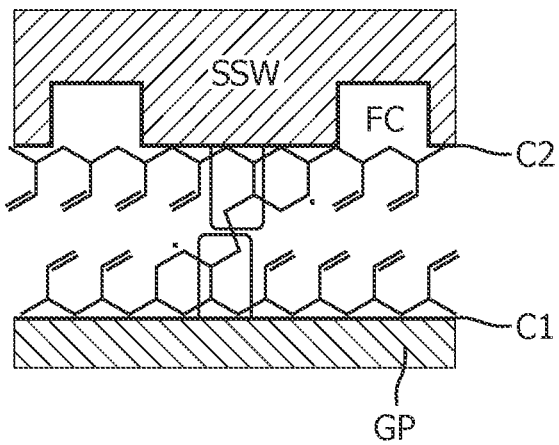
FIG. 5c
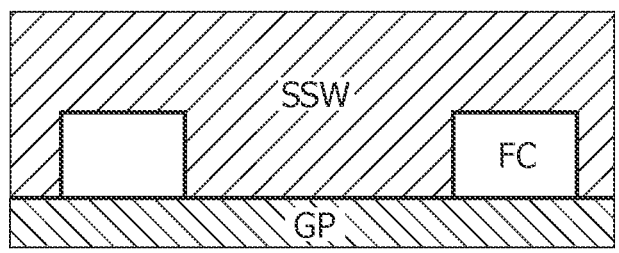
FIG. 5d

GAS CHROMATOGRAPHY COLUMN WITH POLYBUTADIENE COATING

CROSS-REFERENCE TO PRIOR APPLICATIONS

This application is the U.S. National Phase application under 35 U.S.C. § 371 of International Application No. PCT/EP2018/056951, filed on 20 Mar. 2018, which claims the benefit of U.S. Provisional Patent Application No. 62/473551, filed on 20 Mar. 2017. These applications are hereby incorporated by reference herein.

FIELD OF THE INVENTION

The invention relates generally to analysis of gas. Specifically, the invention relates to a gas chromatography (GC) column device and a method for manufacturing a GC column, especially as a micro gas chromatography (μGC) column, such as suited for medical analysis of gas, e.g. breath exhaled from a person or gas based on samples from skin, urine or feces. More specifically, the invention provides a GC column with a first substrate bonded to a second substrate by means of a coating comprising polybutadiene.

BACKGROUND OF THE INVENTION

Exhaled breath analysis in health and disease is an area of growing clinical interest. Using breath as a biological sample is appealing, because breath-collection is cheap, easy to perform and non-invasive. Volatile Organic Compounds (VOCs) are excreted from the skin, urine, feces and most notably via exhaled breath. Besides of pulmonary origin, VOCs may also originate from the blood, reflecting physiological, pathological or pathogen related biochemical processes throughout the body. As such exhaled breath analysis may allow metabolic fingerprinting of disease processes anywhere inside the body.

For analysis of gas samples, such as for the above-mentioned applications, 3D GC columns can be used. A typical μGC column can be comprised of basically two parts: a substrate wafer of silicon with the 3D channel structure and a glass part that covers the channels to form the column. The functional part of such a column is realized by a uniform coating on the sidewalls of the column. The thickness of this coating is typically such as 1 μm, and this thickness must be controlled very well. The assemblage of the substrate and glass parts provides a problem. The glass will not bond onto the coated silicon, since these coatings are mostly based on silanes and siloxanes. This implies that columns may only be filled with the coating as a post assemblage step.

Another problem is the resolution of the coating with respect to the gas components to be separated for detection. For example, in one particular case for breath analysis, it is desired to create a high resolution for Octane and similar molecules over the columns. Detecting Octane in the breath of a person can indicate a certain lunge illness.

SUMMARY OF THE INVENTION

Following the above, the inventors of the present invention have appreciated that it is a problem to be able to provide a GC device, especially a micro GC device, which is capable of providing separation of e.g. Octane as a gas component, and at the same time, the GC device is preferably easy to manufacture at a low cost.

In particular, it may be seen as an object of the present invention to provide a device and method that solves the above mentioned problems, or other problems, of the prior art.

In a first aspect, the invention provides a gas chromatography (GC) column arranged to guide a gas sample from an inlet to an outlet, the column comprising
  a first substrate of a gas tight material, e.g. silicon, the first substrate defining a flow channel in one plane between the inlet at one end and the outlet at an opposite end of the flow channel, wherein the first substrate is coated with a first layer of a first coating material, and
  a second substrate of a gas tight material, e.g. glass, the second substrate being coated with a second layer of a second coating material, wherein the second substrate is bonded to the first substrate by cross-linking between the first and second coating materials, so as to seal the flow channel,
wherein the first and second coating materials comprise polybutadiene to allow said cross-linking, and wherein at least the first coating material comprises an additional material serving to provide a desired molecule selectivity property of flow channel.

Such flow channel forming a GC column is advantageous, since the use of polybutadiene as a coating material allows the first and second substrates to be bonded together by cross-link chemistry. This allows an easy manufacturing process suited for low cost mass production. The easy and low cost manufacturing made possible with such GC column allows the GC column to be considered as a disposable, so that column regeneration is eliminated. Further, modification of the polybutadiene layer with introduction/anchoring of the additional material, such as more polar groups, e.g. unsaturated fatty acids, allows creating or tuning the required molecule selectivity of the column for the specific molecules of interest to be detected, e.g. Octane.

By 'a gas tight material' is understood a material which is gas tight at least to a degree so that the flow channel is functional as a GC column.

In the following, preferred embodiments and features of the first aspect will be described.

The additional material may be selected so as to provide a molecule selectivity of the GC column to allow detection of Octane in the gas sample, hereby allowing detection of lung diseases, e.g. if analyzing a gas sample in the form of exhaled breath from a living person or animal.

The additional material may comprise anchoring or introducing more polar groups to the polybutadiene, e.g. unsaturated fatty acids. Especially, the additional material may comprise linoleic acid which is anchored to the polybutadiene. This allow tuning the GC column to the required resolution for the specific molecules of interest to be detected.

The first and second layers may have a thickness of 0.1 μm to 10 μm, such as 0.5 μm to 2.0 μm, e.g. around 1.0 μm. The first and second layers may have about the same thickness, or it may be preferred that the layers have different thicknesses.

The flow channel may have a width of 1 μm to 300 μm, e.g. 1 μm to 100 μm, and preferably the flow channel also has a depth of 1 μm to 300 μm, e.g. 1 μm to 300 μm. This is suitable for a micro GC which can be made with compact dimensions and e.g. be manufactured in low cost as a disposable.

Especially, the first and second coating materials are identical, however they may be preferred to be different, or at least slightly different. The amount of polybutadiene is preferably in the range 10% to 100%, such as 20% to 95%, such as 30% to 90%, in both of the first and second coating materials in order to obtain the bonding effect.

Preferably, both of the first and second substrates preferably have plane surfaces. In the plane surface of the first substrate, a groove is formed, e.g. by known thin film techniques, wherein the groove defines the flow channel. The plane surface of the second substrate serves to seal the flow channel when bonded to said plane surface of the first substrate. The plane surface of the first subtrate then forms a suitable surface for bonding to the plane surface of the second substrate, thereby providing a good sealing of the flow channel when the two coated materials are bonded together. The first substrate is preferably formed by a material selected from: silicon, glass, ceramics, and metal. The second substrate is preferably also formed by a material selected from: silicon, glass, ceramics, and metal. It may be preferred, that the second substrate formed by a transparent material, such as glass or another gas tight transparent material. In a preferred embodiment, the first substrate is formed by silicon, and the second substrate is formed by glass.

Preferably, the flow channel forms a curved shape in said plane between the inlet and outlet. This allows a GC column with a suitable flow channel length and still with overall compact dimensions. Especially, the curved shape may comprise a zig-zag shaped part with at least 10 bends between the inlet and outlet, so as to utilize a given area to provide a long GC column. Specifically, a length of the flow path between the inlet and outlet is at least a factor of 2 times a distance between the inlet and outlet, such as at least a factor of 10 times a distance between the inlet and outlet.

The first substrate may define a second flow channel in one plane between a second inlet at one end and a second outlet at an opposite end of the second flow channel, thereby providing two GC columns on one substrate. Especially, it may be preferred that a length of the second flow channel is different from a length of the first flow channel.

In a second aspect, the invention provides a disposable gas sample analysis kit comprising a gas chromatography column according to the first aspect. Such disposable kit is advantageous e.g. in a device suitable for performing a analysis of exhaled breath from a living person or animal, or a gas sample based on body fluids, since the GC column based on the first aspect can be manufactured at a low cost to make a disposable kit feasable. Hereby, regeneration of the GC column can be eliminated.

Especially, the GC column, or the described kit, may form part of a breath analysis system comprising a device arranged to receive, for the gas sample obtained from breath exhaled from a subject, chromatographic data indicative of molecule elution times, and a processor programmed to subsequently analyze the chromatographic data for the gas sample in accordance with an analysis algorithm, and to a provide an output accordingly. Sepcifically, the breath analysis system may comprise a gas inlet comprising a mouthpiece arranged on an exterior part of its casing, so as to allow the subject, a person or an animal, to directly breathe into the mouthpiece and thus provide a gas sample to be analysed. Other tube fittings may be used for connection to receive breathed air from a mechanical ventilator, e.g. in intensive care units, to which the subject is connected. Still further, the gas inlet of the device may be arranged for mounting of a gas bag with the gas sample to be analyzed. E.g. the gas inlet may be arranged to receive exhaled breath from a subject, and wherein the GC column according to the first aspect, at least one detector, and a communication module may be arranged within one common casing.

In a third aspect, the invention provides a method of manufacturing a gas chromatography column arranged to guide a gas sample from an inlet to an outlet, the method comprising providing a first substrate of a gas tight material, forming a flow channel on a surface of the first substrate between the inlet and the outlet, coating the first substrate with a first layer of a first coating material comprising polybutadiene and an additional material serving to provide a desired molecule selectivity property of the flow channel, and providing a second substrate of a gas tight material, coating the second substrate with a second layer of a second coating material comprising polybutadiene, and bonding the second substrate to the first substrate by cross-linking between the first and second coating materials, so as to seal the flow channel.

This method is suitable for low cost mass production, since all of the materials involved can be easily made available, and processes involved are also easy to perform and set up in a mass production.

The forming of the flow channel in the silicon substrate water can be performed in a variety of ways, however as known by the skilled person, e.g. various known thin film techniques may be used.

In general, it is appreciated that the various aspects of the invention may be combined and coupled in any way possible within the scope of the invention. These and other aspects, features and/or advantages of the invention will be apparent from and elucidated with reference to the embodiments described hereinafter.

BRIEF DESCRIPTION OF THE DRAWINGS

Embodiments of the invention will be described, by way of example only, with reference to the drawings, in which FIGS. 5a-5d illustrate different steps in the assembly of a silicon substrate wafer and a glass plate with an illustration of the cross-linking bonding between the two coated surfaces of these part.

DESCRIPTION OF EMBODIMENTS

Figure 1:
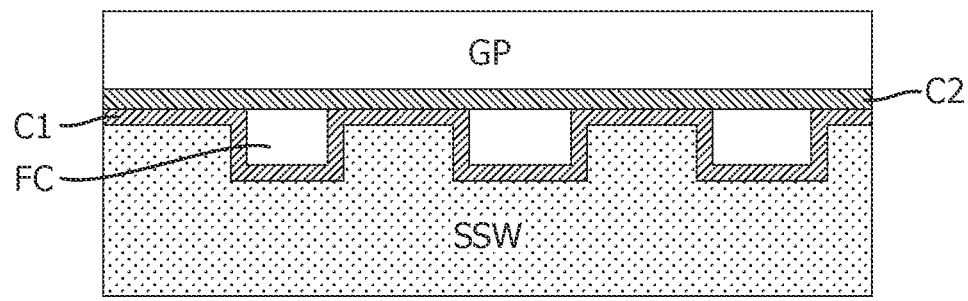
FIG. 1 illustrates a sketch of a section of a GC column embodiment.

FIG. 1 shows a section sketch of a GC column embodiment with a flow channel FC arranged to guide a gas sample from an inlet to an outlet. A first substrate SSW, in preferred embodiments e.g. a silicon substrate wafer, with a plane surface in which a flow channel FC has been formed in one plane between the inlet at one end and the outlet at an opposite end of the flow channel FC. On the sketch, three parts of the flow channel FC are visible, however it is to be understood that the flow channel may have a snake or zig-zag like shape in the plane of the surface of the silicon substrate SSW. E.g. the flow channel FC is made by means of thin film technology to etch the desired shape in the silicon substrate SSW.

The surface of silicon substrate wafer SSW is coated with a first layer C1 of a first coating material. A second substrate GP, preferably a plane glass plate, is coated with a second layer C2 of a second coating material. The glass plate GP is bonded to the silicon substrate wafer SSW by cross-linking between the first and second coating materials and thus the first and second layers C1, C2, so as to seal the flow channel FC. The first and second coating materials comprise polybutadiene to allow said cross-linking effect to provide the bonding between the silicon substrate wafer SSW and the glass plate GP. The first and second layers C1, C2 are preferably formed by coating materials comprising an additional material serving to provide a desired molecule selectivity property of flow channel FC. Especially, the silicon substrate wafer SSW can be spin coated with a solution of polybutadiene rubber in Heptane. After vaporing the Heptane layers of 1 µm±0.5 µm can be deposited. The glass plate GP can also be spin coated with polybutadiene rubber. Both of these polybutadiene rubber layers C1, C2 can effectively cross-link to close the flow channel FC, thereby forming the column. The polybutadiene layer is very hydrophobic. Modification of the hydrophobic layer to more hydrophilic layers can be done by mixing components like unsaturated fatty acids, e.g. linoleic acid, in all kind of ranges. By changing the polarity of the polybutadiene layer the column packing can be tuned for the optimal resolution for the component to be detected, e.g. Octane.

With this choice of materials, the coatings C1, C2 can serve to bond the silicon substrate wafer SSW and the glass plate together, and still it is possible to provide a coating that provides a flow channel coating which can satisfy the requirement to allow tuning the GC column to be able to detect specific molecules. Thus, with the polybutadiene material to provide the bonding effect, it is possible to close the column after having provided the coating which gives the molecule sensitivity.

It is to be understood that the first and second substrates SSW, GP can be made of other materials than silicon and glass, respectively. However, the materials forming the substrates SSW, GP should be gas tight, or at least substantially gas tight in order to be functional as a GC column. E.g. ceramics, or various metals can be used for both the first and second substrates SSW, GP. However, it may be preferred that the second substrate GP is transparent.

The ease for manufacturing leads to a cheap disposable concept for columns for micro GC. The columns do not have to be regenerated, which simplifies this technology. Especially, the GC column may form part of a disposable kit for analyzing gas samples, e.g. based on breath exhaled from a living subject.

Figure 2:
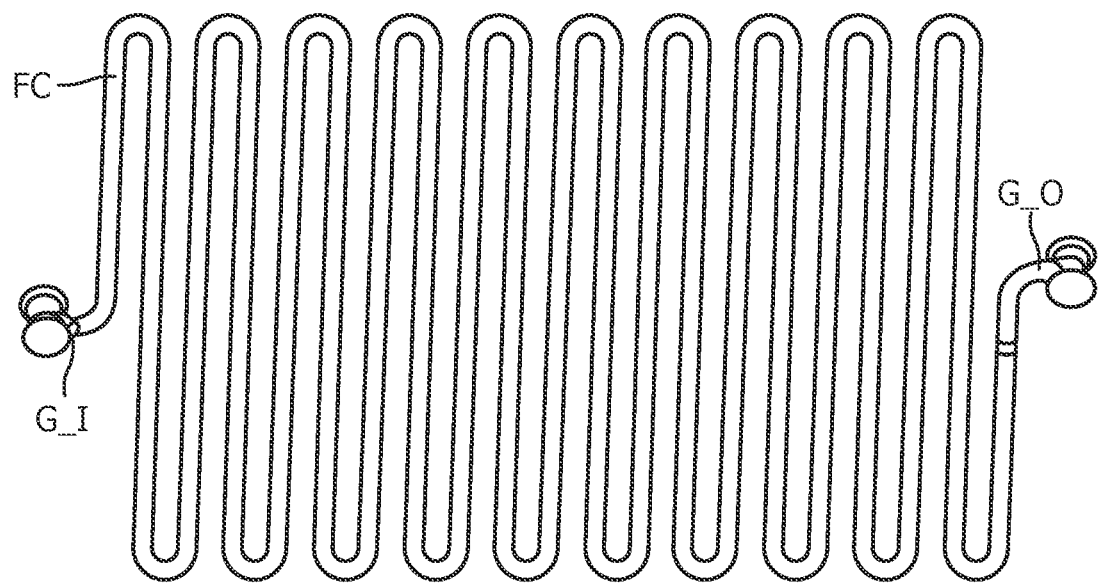
FIG. 2 illustrates a GC embodiment with a zig-zag shaped flow channel.

FIG. 2 shows asketch of an example of a flow channel layout FC between a gas inlet G_I and a gas outlet G_O, where the flow channel FC formed in the surface of the silicon substrate wafer has a zig-zag shape, here shown with at least 10 bends, thereby providing a column length which is significantly longer than the mere distance between gas inlet G_I and outlet G_O.

Figure 3:
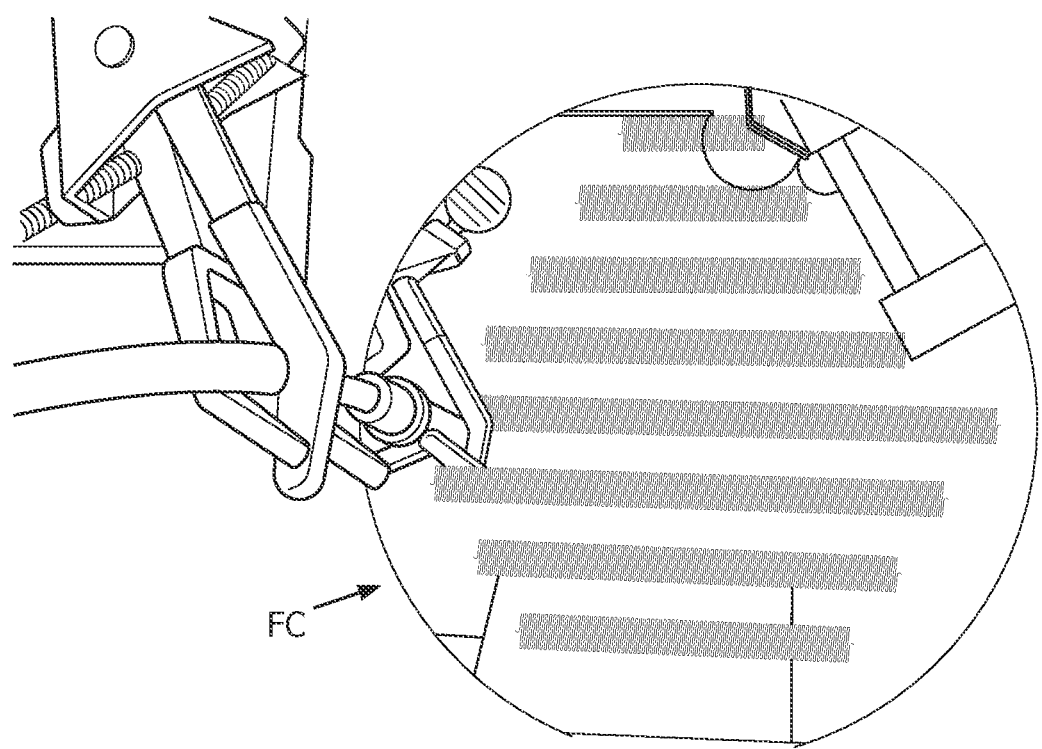
FIG. 3 illustrates a photo of a GC embodiment with 7 separate flow channels with different lengths.

FIG. 3 shows a photo of a GC column embodiment with a plurality of separate zig-zag shaped flow channels, each with separate gas inlet and outlets. The number of zig-zag bends are different in the separate flow channels, thereby providing different effective column lengths. In the shown photo there are 7 separate flow channels arranged in a parallel pattern.

Figure 4:
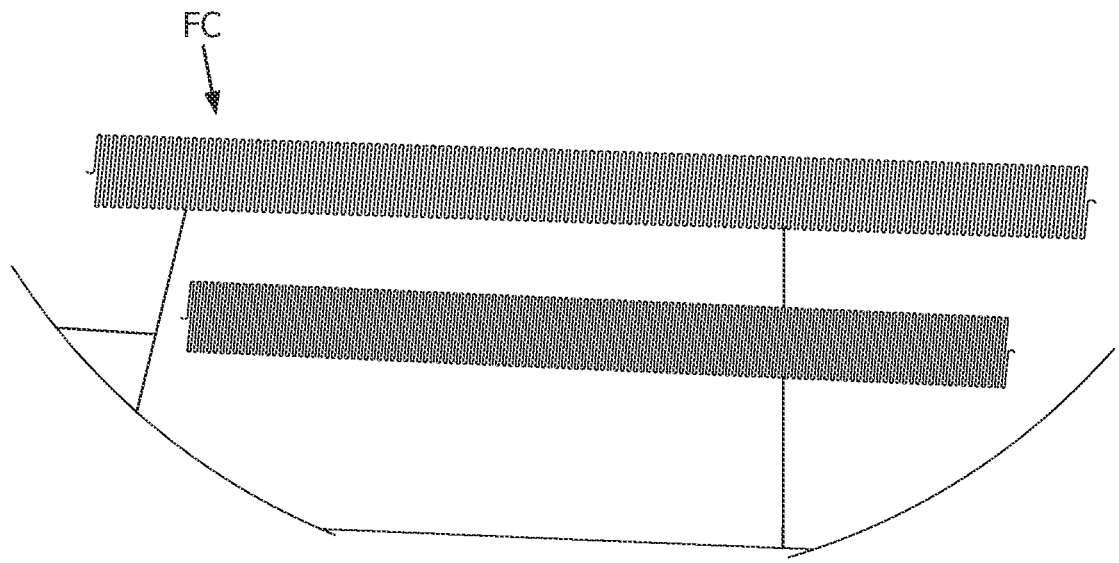
FIG. 4 illustrates a photo of two zig-zag shaped flow channels of different lengths.

FIG. 4 shows a photo of two of the separate parallel flow channels of the photo of FIG. 3 are shown in more details, where the zig-zag or snake pattern with a plurality of bends can be seen.

FIGS. 5a-5d shows steps of a process of assembly of a GC column. A plane glass plate GP and a plane silicon substrate wafter SSW with a flow channel FC defined on its surface have been coated with respective coatings C1, C2 which both comprise polybutadiene. In FIG. 5a the two parts GP, SSW have not yet been put together. In FIGS. 5b and 5c, the two parts GP, SSW are put so close together, that their polybutadiene coatings C1, C2 provide a cross-linking serving to bond the two parts GP, SSW together. This cross linking can be formed in many ways. In FIG. 5b shows one example of cross linking, namely a block square bond between the Carbon atoms in the poybutadiene coatings C1, C2 is indicated as a cross linking possibility. In FIG. 5c another cross linking possibility is indicated, which is more likely formed, namely where two free electrons can further initiate polymerization between the two polybutadiene coating layers C1, C2. In FIG. 5d, the two parts GP, SSW have been bonded together, so as to seal the flow channel FC, thereby forming a GC column. In preferred micro GC columns embodiments, the flow channel FC has depth and width dimension of 1 µm to 300 µm, e.g. 1 µm to 100 µm, such as 1 µm to 50 µm. E.g. depth and width dimensions may be similar or substantially similar, such as in a specific example, a depth of 2 µm and a width of 3 µm. However, it is to be understood that the principle of the invention can be used also for flow channel FC dimensions much larger than 300 µm as well.

Figure 6:
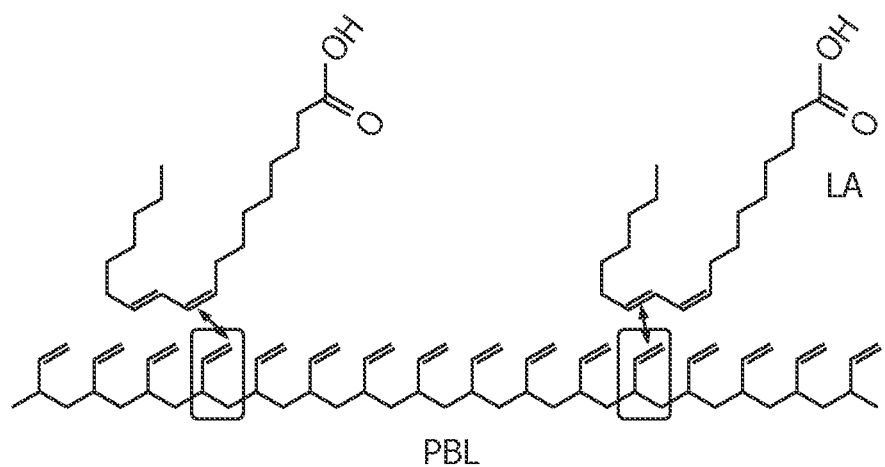
FIG. 6 illustrates anchoring of linoleic acid into the coating polybutadiene rubber layer.

FIG. 6 shows anchoring an additional material to the polybutadiene rubber layer PBL, namely in this example linoleic acid. This material changes the polarity of the polybutadiene rubber layer PBL, and therefore effectively changes the flow channel properties, and still the bonding effect can be preserves. E.g. the use of linoleic acid can allow detection of Octave with the GC column.

Figure 7:
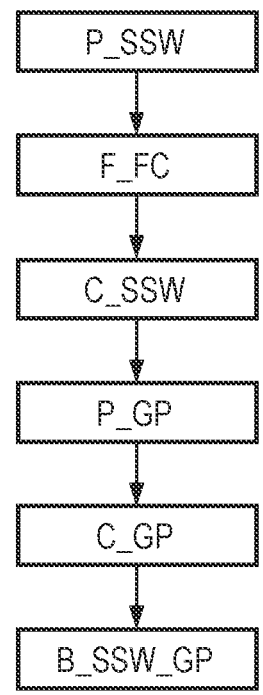
FIG. 7 illustrates steps of a method embodiment.

FIG. 7 shows steps of an embodiment of a method of manufacturing a GC column arranged to guide a gas sample from an inlet to an outlet. The method comprises providing a silicon substrate wafer P_SSW and providing a glass plate P_GP. Using e.g. thinfilm techniques, the method comprises forming F_FC a flow channel on a surface of the silicon substrate wafer between the inlet and the outlet. Next step is coating C_SSW of the silicon substrate wafer with a first layer of a first coating material comprising polybutadiene and an additional material serving to provide a desired molecule selectivity property of the flow channel. Then, coating C_GP the glass plate with a second layer of a second coating material comprising polybutadiene, and finally, bonding (B_SSW_GP) the glass plate to the silicon substrate wafer by cross-linking between the first and second coating materials, so as to seal the flow channel. The first and second coating materials may be identical, and preferably the coating material comprises an additional material to provide a desired molecule detection effect.

It is understood that the GC column of the invention may be used in connection with analysis of the medical data, e.g. diagnosing a disease based on a result of analysing exhaled breath from a subject according to the gas sample synchronizing method. The method may further comprise initiating a specific therapy, e.g. a medical treatment of Tuberculosis. Further, breath VOC analysis may be used for monitoring/analysis of lung cancer, breast cancer, other types of cancer, or respiratory infections. Also, breath analysis may be applicable for monitoring diseases such as asthma and Chronic Obstructive Pulmonary Disease (COPD) e.g. reponse to treatment, excacerbation monitoring. Especially, this may involve detecting molecules such as Octane. Furthermore, breath analysis may further be applied for monitoring glucose level in diabetes. Still further, an application example may be monitoring for sepsis and necrotizing enterocolitis (NEC) from VOC analysis based on gas analysis based on feces in neonates.

In general, applications of the GC column according to the invention may be within the fields of such as Breath analysis, Oncology, Wound treatment, Food conservation and Urine tests.

To sum up, the invention provides a 3D gas chromatography (GC) column development is possible by assembly of two parts each being substrates formed by gas tight materials. One part may be a silicon substrate with a snake shaped flow channel structure and the other part may be a glass plate. Both are coated with a column packing comprising polubutadiene, which is also able to glue or bond both parts together, thereby sealing the flow channel, thus forming a GC column. The column packaging can be composed in all kinds of polarity from very hydrophobic till very hydrophilic. In this way the column packing can be tuned on resolution for particular molecules which are interesting to detect, e.g. Octane. The invention is advantageous for micro GC columns.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A gas chromatography column arranged to guide a gas sample from an inlet to an outlet, the gas chromatography column comprising
    a first substrate of a gas tight material, the first substrate defining a flow channel in one plane between the inlet at one end and the outlet at an opposite end of the flow channel, wherein the first substrate is coated with a first layer of a first coating material; and
    a second substrate of a gas tight material, the second substrate being coated with a second layer of a second coating material, wherein the second substrate is bonded to the first substrate by cross-linking between the first and second coating materials, so as to seal the flow channel,
    wherein the first and second coating materials comprise polybutadiene to allow the cross-linking, and wherein at least the first coating material comprises an additional material introduced to the polybutadiene serving to tune molecule selectivity to provide a desired molecule selectivity property of the flow channel for specific molecules of interest to be detected.

2. The gas chromatography column according to claim 1, wherein the molecule selectivity of the additional material allows detection of Octane in the gas sample.

3. The gas chromatography column according to claim 1, wherein the additional material comprises linoleic acid which is anchored to the polybutadiene.

4. The gas chromatography column according to claim 1, wherein the first and second layers have a thickness of 0.1 μm to 10 μm.

5. The gas chromatography column according to claim 1, wherein the flow channel has a width of 1 μm to 300 μm.

6. The gas chromatography column according to claim 1, wherein the first and second coating materials are identical.

7. The gas chromatography column according to claim 1, wherein the first substrate has a plane surface in which a groove has been formed, wherein the groove defines the flow channel, and wherein the second substrate has a plane surface arranged to seal the flow channel when bonded to said plane surface of the first substrate.

8. The gas chromatography column according to claim 1, wherein the flow channel forms a curved shape in said plane between the inlet and outlet.

9. The gas chromatography column according to claim 1, wherein the first substrate is formed by silicon, glass, ceramics, or metal.

10. The gas chromatography column according to claim 1, wherein the second substrate is formed by silicon, glass, ceramics, or metal.

11. The gas chromatography column according to claim 1, wherein the first substrate is formed by silicon, and wherein the second substrate is formed by glass.

12. The gas chromatography column according to claim 1, wherein a length of a flow path between the inlet and the outlet is at least a factor of 2 times a distance between the inlet and the outlet.

13. The gas chromatography column according to claim 1, wherein the first substrate defines a second flow channel in one plane between a second inlet at one end and a second outlet at an opposite end of the second flow channel.

14. A disposable gas sample analysis kit comprising the gas chromatography column according to claim 1.

15. The gas chromatography column according to claim 1, wherein a length of a flow path between the inlet and outlet is at least a factor of 10 times a distance between the inlet and outlet.

16. A method of manufacturing a gas chromatography column arranged to guide a gas sample from an inlet to an outlet, the method comprising:
    providing a first substrate of a gas tight material;
    forming a flow channel on a surface of the first substrate between the inlet and the outlet;
    coating the first substrate with a first layer of a first coating material comprising polybutadiene and an additional material serving to tune molecule selectivity to provide a desired molecule selectivity property of the flow channel for specific molecules of interest to be detected;
    providing a second substrate of a gas tight material;
    coating the second substrate with a second layer of a second coating material comprising polybutadiene; and
    bonding the second substrate to the first substrate by cross-linking between the first and second coating materials, so as to seal the flow channel.

17. A gas chromatography column arranged to guide a gas sample from an inlet to an outlet, the gas chromatography column comprising a first substrate formed of silicon, glass, ceramics or metal, the first substrate defining a flow channel in one plane between the inlet at one end and the outlet at an opposite end of the flow channel, wherein the first substrate is coated with a first layer of a first coating material; and a second substrate formed of silicon, glass, ceramics or metal, the second substrate being coated with a second layer of a second coating material, wherein the second substrate is bonded to the first substrate by cross-linking between the first coating material and the second coating material to seal the flow channel, wherein the first coating material and the second coating material comprise polybutadiene to enable the cross-linking, and wherein the first coating material and the second coating material provide a flow channel coating of the flow channel.

18. The gas chromatography column according to claim 17, wherein the first substrate is formed of silicon and the second substrate is formed of glass.

19. The gas chromatography column according to claim 17, wherein the first substrate has a plane surface in which a groove has been formed, wherein the groove defines the flow channel, and wherein the second substrate has a plane surface arranged to seal the flow channel when bonded to the plane surface of the first substrate.

20. The gas chromatography column according to claim 17, wherein at least one of the first coating material and the second coating material comprises an additional material to the polybutadiene serving to tune molecule selectivity to provide a desired molecule selectivity property of the flow channel for specific molecules of interest to be detected.

\* \* \* \* \*